United States Patent
Beil et al.

(10) Patent No.: US 9,801,445 B2
(45) Date of Patent: Oct. 31, 2017

(54) CONTAINER FOR ACCOMMODATING AN OPHTHALMIC LENS DURING A LENS TREATMENT PROCESS

(71) Applicant: Novartis AG, Basel (CH)

(72) Inventors: Roger Beil, Aschaffenburg (DE); Katrin Sylke Struckmeier, Aschaffenburg (DE); Jan Bernard, Niedernberg (DE); Andrea Kopp, Aschaffenburg (DE)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 15/274,079

(22) Filed: Sep. 23, 2016

(65) Prior Publication Data

US 2017/0086553 A1   Mar. 30, 2017

Related U.S. Application Data

(60) Provisional application No. 62/232,636, filed on Sep. 25, 2015.

(51) Int. Cl.
*A45C 11/00* (2006.01)
*B05C 13/00* (2006.01)
(Continued)

(52) U.S. Cl.
CPC ............... *A45C 11/005* (2013.01); *B05C 3/02* (2013.01); *B05C 3/10* (2013.01); *B05C 13/00* (2013.01);
(Continued)

(58) Field of Classification Search
CPC . A45C 11/005; A45C 11/046; B29D 11/0023; B29D 11/00125;
(Continued)

(56) References Cited

U.S. PATENT DOCUMENTS 3,621,855 A   11/1971   Rabinowitz
3,661,248 A    5/1972   Isen
(Continued)

FOREIGN PATENT DOCUMENTS

WO   2011045380 A1   4/2011
WO   2011045384 A1   4/2011

OTHER PUBLICATIONS

International Searching Authority, International Search Report and Written Opinion, PCT/IB2016/055714, Nov. 21, 2016.

*Primary Examiner* — Laura Edwards
(74) *Attorney, Agent, or Firm* — Robert A. Ambrose

(57) ABSTRACT

A container (1) for accommodating an ophthalmic lens during a lens treatment process has a longitudinal axis (11) and comprises as separate elements a containment element (2), a mounting element (3), and a retaining element (4). The containment element (2) comprises a tubular section (21) and a bottom (22) arranged at a distal end of the tubular section (21), the bottom (22) protruding convexly towards the outside at the distal end of the tubular section (21) and being provided with a number of apertures (23, 24), the tubular section (21) at a proximal end (25) thereof having a latch (26) protruding from the proximal end (25) of the tubular section (21) towards the mounting element (3). The mounting element (3) comprises a sidewall (31) extending along the longitudinal axis (11) of the container (1), the sidewall (31) being provided with recesses or orifices (32) which are in engagement with the latch (26) of the containment element (2). The mounting element (3) further comprises an access opening (37) arranged at a proximal end of the mounting element (3) remote from the containment element (2). The retaining element (4) is fixedly arranged in between the containment element (2) and the mounting element (3), the retaining element (4) being configured to prevent the ophthalmic lens from being washed out of the (Continued)

containment element (2) and to permit access for a gripper through the access opening (37) of the mounting element (3) into the containment element (2) for insertion and removal of the ophthalmic lens.

18 Claims, 7 Drawing Sheets

(51) Int. Cl.
  *B05C 13/02*   (2006.01)
  *B05C 3/10*   (2006.01)
  *B05C 3/02*   (2006.01)
  *B29D 11/00*   (2006.01)
  *A61L 12/00*   (2006.01)
  *G02C 13/00*   (2006.01)
  *A45C 11/04*   (2006.01)
  *A61L 12/08*   (2006.01)

(52) U.S. Cl.
  CPC ........ *B05C 13/025* (2013.01); *B29D 11/0023* (2013.01); *B29D 11/00067* (2013.01); *B29D 11/00125* (2013.01); *A45C 11/046* (2013.01); *A61L 12/00* (2013.01); *A61L 12/08* (2013.01); *A61L 12/086* (2013.01); *B65D 2585/545* (2013.01); *G02C 13/008* (2013.01)

(58) Field of Classification Search
  CPC ........ B29D 11/00067; B65D 2585/545; A61L 12/00; A61L 12/086; A61L 12/08; G02C 13/008
  USPC ........ 118/423, 428, 429, 500; 422/292, 294; 206/5.1; 134/901; 427/169, 2.1
  See application file for complete search history.

(56) References Cited

U.S. PATENT DOCUMENTS

| | | |
|---|---|---|
| 4,721,124 A | 1/1988 | Tuerkheimer |
| 2003/0222362 A1* | 12/2003 | Indra ...................... A61L 12/04 264/2.6 |
| 2010/0072082 A1 | 3/2010 | Kang |
| 2011/0089053 A1 | 4/2011 | Biel |
| 2012/0126558 A1 | 5/2012 | Lässig |
| 2012/0152284 A1 | 6/2012 | Winterton |
| 2013/0220855 A1 | 8/2013 | Markovitch |
| 2014/0174956 A1 | 6/2014 | Biel |
| 2015/0209819 A1 | 7/2015 | Biel |

* cited by examiner

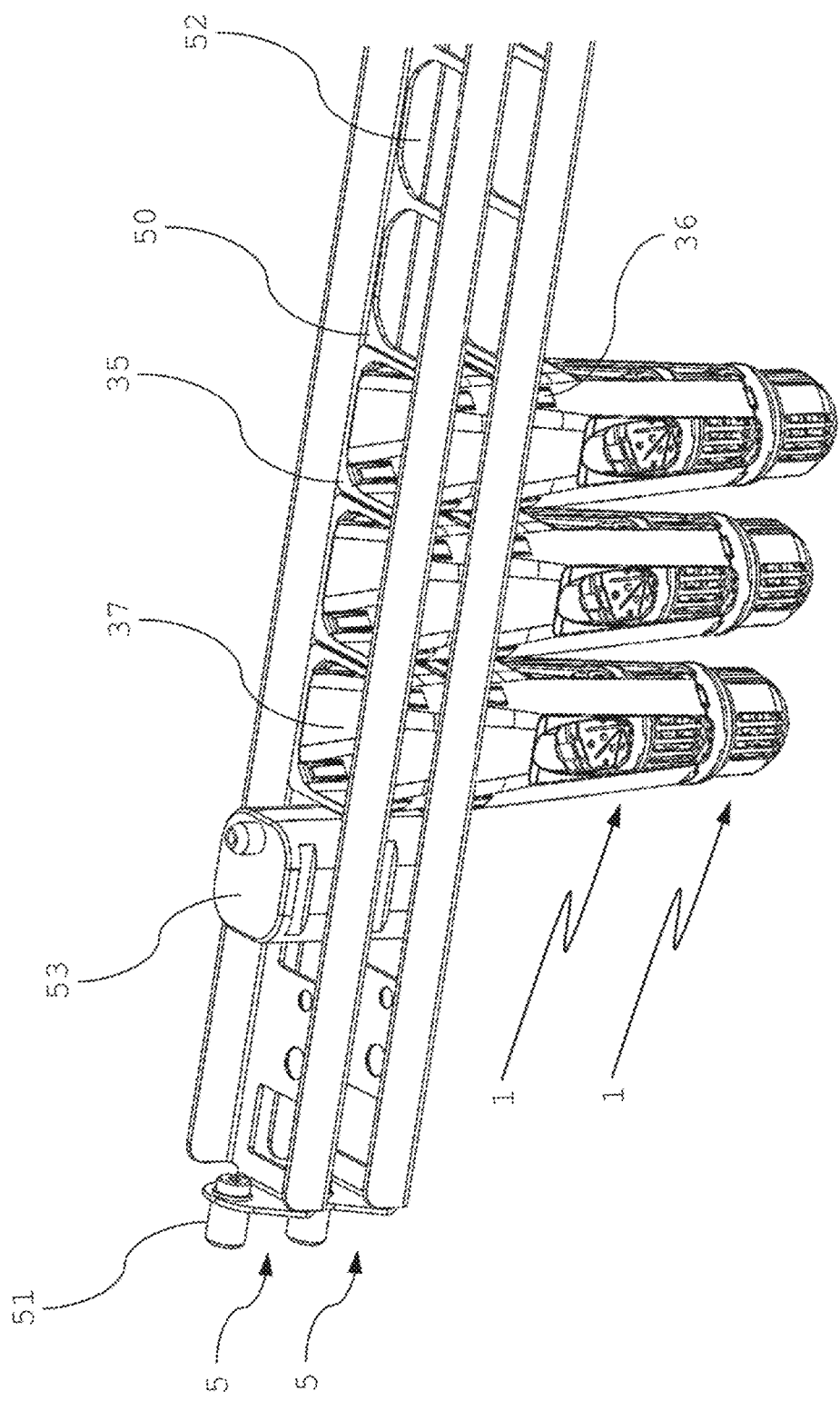

CONTAINER FOR ACCOMMODATING AN OPHTHALMIC LENS DURING A LENS TREATMENT PROCESS

FIELD

The present invention relates to a container for the accommodation of an ophthalmic lens during a treatment process.

BACKGROUND

Ophthalmic lenses, such as contact lenses, particularly soft contact lenses, are generally manufactured in automated production processes well known in the art. Depending on the lens forming materials used and according to the production method applied, the contact lenses have to be immersed in specific treatment liquids such as extraction liquids, rinsing liquids, coating liquids, etc., to obtain the final contact lens which is suitable to be worn in direct contact with the wearer's eye. For that purpose it is known to transport the contact lenses through several baths containing such treatment liquids. For example, the contact lenses are introduced into containers arranged in a transport carrier which is moved along the length of the individual baths such that the contact lenses contained in the respective containers are exposed to the treatment liquid of the respective bath. Movement of the transport carrier is performed such that the contact lens in the respective container always is in contact with the treatment liquid of the respective bath. After having passed through one bath, the containers arranged in the transport carrier are transferred to a further treatment bath containing a further treatment liquid.

US 2011/0089053 A1 discloses a container for the accommodation of a contact lens during a lens treatment process such as extraction and/or rinsing and/or coating processes. The container is molded in one piece and comprises an elongated tubular body with a sidewall, and further comprises at a distal end thereof a bottom which protrudes convexly towards the outside. The bottom is provided with a number of apertures which enable flow of a liquid into and out of the tubular body. A retaining element is arranged inside the tubular body which is attached inside the tubular body by means of lugs engaging in corresponding apertures in the sidewall of the tubular body. The retaining element is flexible and allows access of a transfer means into the tubular body towards the bottom thereof for insertion and removal of a contact lens, and also enables a free rising of the liquid inside the tubular body while at the same time preventing the contact lens from being washed out of the tubular body.

US 2014/174956 A1 discloses a similar container having a leg portion comprising four legs (extending along the longitudinal axis of the container) and a convex containment portion at the distal end of the container to hold the contact lens during the transport of the contact lens through the various baths. A retainer ring is arranged inside the leg portion and clamps the circumferential portion of a retaining element against the inner sidewall of the leg portion of the container. The container is molded in one piece. Between the legs of the leg portion flow openings are arranged, so that the container allows for a stacked arrangement of containers in which the bottom portion of one container is arranged within the leg portion of another container and still allows for a good contact of the contact lens held in the containment portion of the "inner" container with the treatment liquid.

SUMMARY

It is therefore an object of the invention to further improve efficiency of the treatment of ophthalmic lenses, in particular contact lenses such as soft contact lenses, in liquid baths. It is a further object of the invention to improve the processes and apparatuses used for the treatment of the lenses in liquid baths.

To achieve these objects, the present invention suggests a device as it is specified by the features of the independent claim. Advantageous aspects of the device according to the invention are the subject matter of the dependent claims.

In the instant application, the terms "distal" and "proximal" refer to the position of the container and its elements under typical operating conditions. Specifically, the term "distal" refers to the respective lower part of the container or element considered, whereas the term "proximal" refers to the upper part of the container or element considered.

In particular, the invention suggests a container for accommodating an ophthalmic lens during a lens treatment process, the container having a longitudinal axis. The container comprises as separate elements a containment element, a mounting element, and a retaining element. The containment element comprises a tubular section and a bottom arranged at a distal end of the tubular section, the bottom protruding convexly towards the outside at the distal end of the tubular section. The bottom is provided with a number of apertures for enabling a free flow of a treatment liquid into and out of the containment element. The tubular section at a proximal end thereof has a latch protruding from the proximal end of the tubular section towards the mounting element. The mounting element comprises a sidewall extending along the longitudinal axis of the container. The sidewall is provided with recesses or orifices which are in engagement with the latch of the containment element. The mounting element further comprises an access opening arranged at a proximal end of the mounting element. The retaining element is fixedly arranged in between the containment element and the mounting element. The retaining element is configured to prevent the ophthalmic lens from being washed out of the containment element and to permit access for a gripper through the access opening of the mounting element into the containment element for insertion and removal of the ophthalmic lens.

According to one aspect of the device according to the invention, the mounting element further comprises a plurality of elongated flow openings arranged in the sidewall for allowing a treatment liquid to flow into and out of an inner space of the mounting element.

According to a further aspect of the device according to the invention, the elongated flow openings are tapering, particularly in an elliptic shape, towards a proximal end thereof.

According to a still further aspect of the device according to the invention, the retaining element comprises a through-hole arranged in a circumferential portion of the retaining element, with the latch of the containment element extending through the through-hole of the retaining element.

According to yet a further aspect of the device, the mounting element has at least one lug protruding in longitudinal direction from a distal end of the mounting element towards the proximal end of the tubular section of the containment element, and the retaining element has at least one indentation arranged in a circumferential portion of the retaining element, with the at least one lug of the mounting element engaging into the at least one indentation of the retaining element.

Still in accordance with another aspect of the device according to the invention, the sidewall of the mounting element extends along the longitudinal axis of the container from the access opening to the proximal end of the tubular section of the containment element and defines an inner space of the mounting element which allows for introduction of the containment element of another such container into the inner space of the mounting element of the container through the access opening.

In accordance with a further aspect of the device according to the invention, the sidewall of the mounting element is arranged to conically taper towards the distal end of the mounting element.

According to a further aspect of the device according to the invention, the mounting element is provided with a flange surrounding the access opening, the flange having a square shape.

According to a still further aspect of the device according to the invention, the sidewall of the mounting element is provided with at least one resilient locking tab arranged beneath the flange.

Yet in accordance with another aspect of the device according to the invention, the retaining element comprises a diaphragm having flexible fins which extend from a circumferential portion of the retaining element towards a center of the diaphragm. The flexible fins are inclined towards the bottom of the containment element and are provided with fin through-holes for enabling free passage of treatment liquid into and out of the containment element.

In accordance with a still further aspect of the device according to the invention, the apertures in the containment element comprise bottom through-holes and longitudinal slots, the longitudinal slots extending from the bottom into the tubular section towards the proximal end of the tubular section of the containment element.

Yet in accordance with another aspect of the device according to the invention, at least on an inner surface of the bottom of the containment element the apertures open out into the inner surface of the bottom with rounded edges.

A further aspect of the invention relates to a transport carrier comprising an elongated web as well as two engagement portions capable of engaging with a transport device. One of the two engagement portions is arranged at one longitudinal end of the elongated web and the other one of the two engagement portions is arranged at the other end of the elongated web. The transport carrier further comprises a plurality of adjacently arranged through-holes in the elongated web, with at least one container according to the invention being arranged in the through-holes of the elongated web of the transport carrier, in particular with a container according to the invention being arranged in each of the through-holes of the elongated web of the transport carrier.

An additional aspect of the invention relates to a transport carrier assembly comprising at least two transport carriers according to the invention arranged in a manner stacked one above the other. The at least two transport carriers are stacked one above the other such that the containment element of the at least one container according to the invention arranged in the through-holes of the web of the respective upper transport carrier is arranged in the inner space of the mounting element of a container according to the invention arranged in the through-holes of the respective lower transport carrier, in particular with each containment element of the containers according to the invention arranged in each of the through-holes of the elongated web of the upper transport carrier being arranged in the inner space of the mounting element of each of the containers according to the invention arranged in the through-holes of the web of the lower transport carrier.

Due to the multipart construction, the dimensions of the container according to the invention are more flexible. For example, the container may have an increased length (viewed in direction of its longitudinal axis) in order to ensure that the containment element (holding the ophthalmic lens) is always completely immersed in the treatment baths, even when the treatment baths have different levels of treatment liquid. The enhanced construction thus allows for reliable immersion of the contact lens even with lateral transportation of the carrier in which the container is arranged and if the levels of treatment liquids in the baths are different. Additionally, due to the smaller dimensions of the individual separate elements of the container according to the invention reliability of the manufacture of the separate elements is enhanced while at the same time assembly of the container is simple. The latch engages with the recesses or orifices of the mounting element and holds the retaining element in between the containment element and the mounting element.

The mounting element allows for a secure mounting of the container to a transport carrier with the aid of which a plurality of such containers each containing a lens can be transported together through one or more liquid baths. The mounting element allows the containers to be mounted to the transport carrier such that the containment element is immersed in the treatment liquid while the transport carrier is not immersed in the treatment liquid.

The elongated flow openings arranged in the sidewall allow for flow of treatment liquid into and out of the inner space of the mounting element, hence allowing for a continuous exchange of treatment liquid during movement and transportation of the container through the baths.

The container is stackable, that is to say another container of the same type can be introduced through the access opening at the longitudinal end of the mounting element remote from the containment element (i.e. at the proximal end of the container) into the mounting element to form two containers stacked one within the other. At the same time, however, a good flow of treatment liquid is still ensured into the containment element of the "inner" container of the stacked containers to provide for a good exposure of the ophthalmic lenses contained in the containment elements of both stacked containers.

This provides for a plurality of advantages. For example, if the transportation speed of the containers containing the lenses remains unchanged and two stacked containers are transported through the liquid bath instead of one, the number of ophthalmic lenses that can be treated in the same period of time is twice as much. In case of three stacked containers, the number of lenses that can be treated in the same period of time is three times as much. Alternatively, if the number of ophthalmic lenses to be treated (i.e. the number of ophthalmic lenses transported through a bath) during a predetermined period of time is to remain unchanged, in case of two stacked containers it is possible to reduce the transportation speed to one half of the transportation speed of the conventional transportation speed. This may be advantageous in that the lenses are exposed to the treatment liquid for a longer period of time which is twice as long. For example, in case of exposure of the ophthalmic lenses to an extraction liquid the completeness of extraction can thus be further improved. Alternatively, the baths may be of smaller constructional size so that the exposure time of the ophthalmic lens to the treatment liquid is kept constant due to the slower transportation speed through the treatment baths. Hence, the size of the treatment line within the manufacturing line may be more compact.

Similar considerations hold for rinsing, coating and other treatment processes. In both cases (number of ophthalmic lenses to be treated in a predetermined period of time is increased, number of ophthalmic lenses to be treated in a period of time is unchanged but exposure time of the lenses to the liquid is increased) there is no need to make any constructional changes to an already existing apparatus.

In particular, this method also allows for a better and more flexible customization of the production steps or the manufacturing line. For example, in case the space consumption of a manufacturing line is to be decreased while the number of lenses to be treated in a predetermined period of time is to remain unchanged, the transportation speed may be decreased down to one half, one third or less of the original transportation speed, and the length of the liquid baths (in the direction of transport) can be shortened down to one half, one third or less of the original length.

The tapering flow openings reduce the risk that the stacked containers get blocked or interlocked upon removing the stacked second container (the "inner" container) from the inner space of the first container (the "outer" container).

The through-hole at the circumferential portion of the retaining element is designed such that the latch of the containment element extends through the through-hole when the container is assembled. Thus, the latch also holds the retaining element in position.

Similarly, the lug protruding in longitudinal direction from the distal end of the mounting element towards the proximal end of the containment element engages into a corresponding indentation of the retaining element and holds the retaining element in position.

Both measures contribute to a secure mounting of the retaining element in between the mounting element and the containment element when the container is assembled.

The sidewalls of the mounting element conically taper outwardly towards the distal end of the mounting element and thus allow for easy insertion (stacking) of another container through the access opening into the mounting element to form a stack of two containers. Furthermore, this conical taper simplifies insertion of the container (from above) into a through-hole of a transport carrier (where it can be secured with a snap-fit, for example).

The square flange surrounding the access opening at the proximal end of the mounting element allows for insertion of the container into a through-hole provided in a transport carrier until the flange abuts against the transport carrier when introduced in the through-hole thereof so that the container is securely mounted onto the transport carrier. The square shape of the flange permits that a plurality of containers can be arranged next to each other at a very small distance along the length of the transport carrier.

The resilient locking tabs arranged underneath the square shaped flange in the sidewalls of the mounting element allow for an easy securing of the container to the transport carrier by insertion of the container into the through-hole of the carrier. The locking tabs then securely attach the respective container to the transport carrier (snap-fit).

The bottom through-holes and the longitudinal slots in the containment element allow treatment liquid to enter and exit the containment element, where the ophthalmic lens is entrapped while freely floating in the treatment liquid in the containment element.

The flexible fins enable an easy insertion of a gripper or for the insertion and removal of an ophthalmic lens into or from the containment element. Upon insertion of the gripper, the fins bend downwardly towards the bottom of the container. Due to their flexibility they move back to their original retaining position after the gripper has been withdrawn. The fin through-holes enable a free flow of liquid therethrough.

The apertures at the inner surface of the bottom of the containment element opening out into the inner surface of the bottom are provided with rounded edges that allow additional protection of the ophthalmic lens during processing. The rounded edges, in contrast to "sharp" edges, minimize the risk that the ophthalmic lens is getting damaged when coming into contact with such edge during its floating movement in the containment element.

It is to be noted, that every individual feature described herein as well as all combination of two or more of such features are possible as long as such features are not mutually exclusive or are otherwise technically incompatible.

BRIEF DESCRIPTION OF THE DRAWINGS

Embodiments of the container and transport carrier and transport carrier assembly according to the invention are described in more detail with reference to the accompanying drawings, in which:

FIG. 7 is a perspective view of an embodiment of a transport carrier assembly according to the invention with two transport carriers stacked one above the other.

DETAILED DESCRIPTION OF EMBODIMENTS

As used in this specification, the term "treatment liquid" or "treatment liquids" comprises any type of liquid to which the ophthalmic lens, in particular a contact lens such as a soft contact lens, may be exposed during a contact lens manufacturing process, and include in particular liquids influencing the physical or chemical properties of the lens. Without being exhaustive, such treatment liquids may comprise extraction liquids, rinsing liquids, coating liquids or any other type of liquid and in particular also may comprise water.

The term "along the longitudinal axis of the main body" is used to describe the general direction in which the mounting element of the container extends. Although possible, the mounting element does not have to run exactly parallel to the longitudinal axis, and in particular the mounting element has a slightly conical shape.

Figure 1:
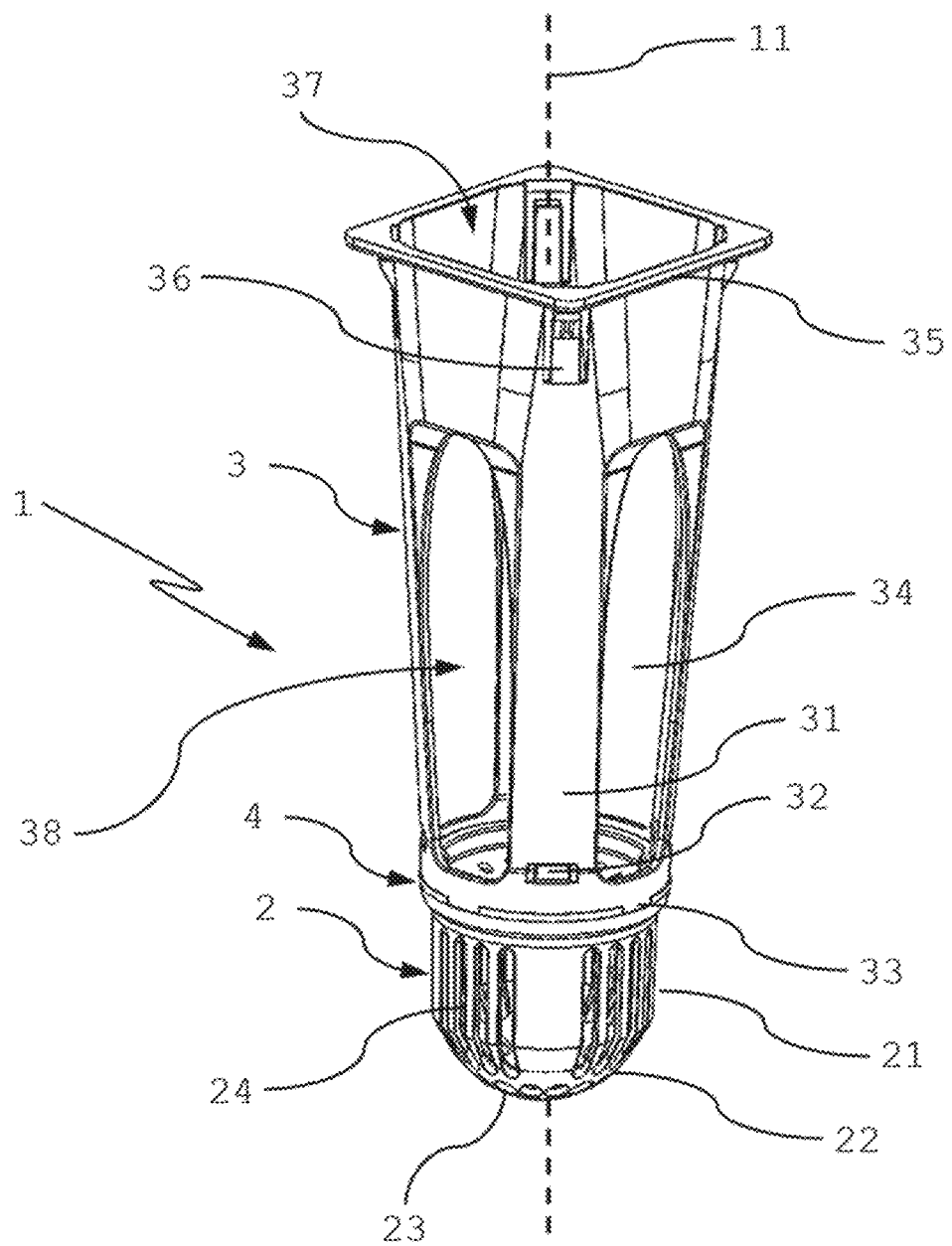
FIG. 1 is a perspective view of an embodiment of the container according to the invention.
Figure 2:
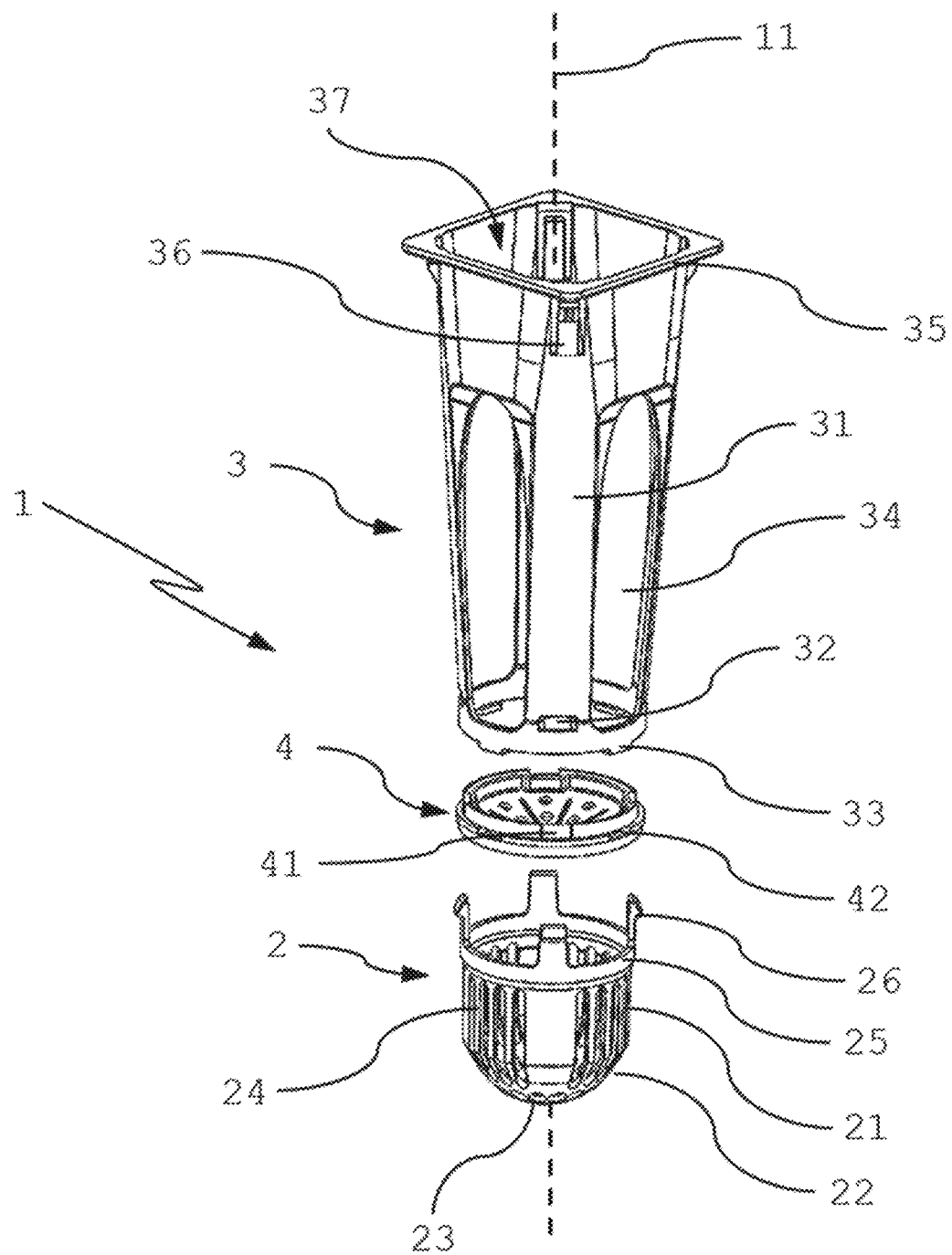
FIG. 2 is an exploded view of the container of FIG. 1.

FIG. 1 shows a perspective view of an embodiment of an assembled container 1 according to the invention, and FIG. 2 shows an exploded view of the embodiment of container 1 of FIG. 1. Container 1 comprises separate elements, namely a containment element 2, a mounting element 3, and a retaining element 4. Mounting element 3 comprises elongated flow openings 34 for allowing the treatment liquid to enter into and exit an inner space of mounting element 3, the inner space of mounting element 3 being surrounded by a sidewall 31 in which the elongated flow openings 34 are arranged. Container 1 further comprises a retaining element 4 fixedly arranged in between containment element 2 and mounting element 3.

Figure 3:
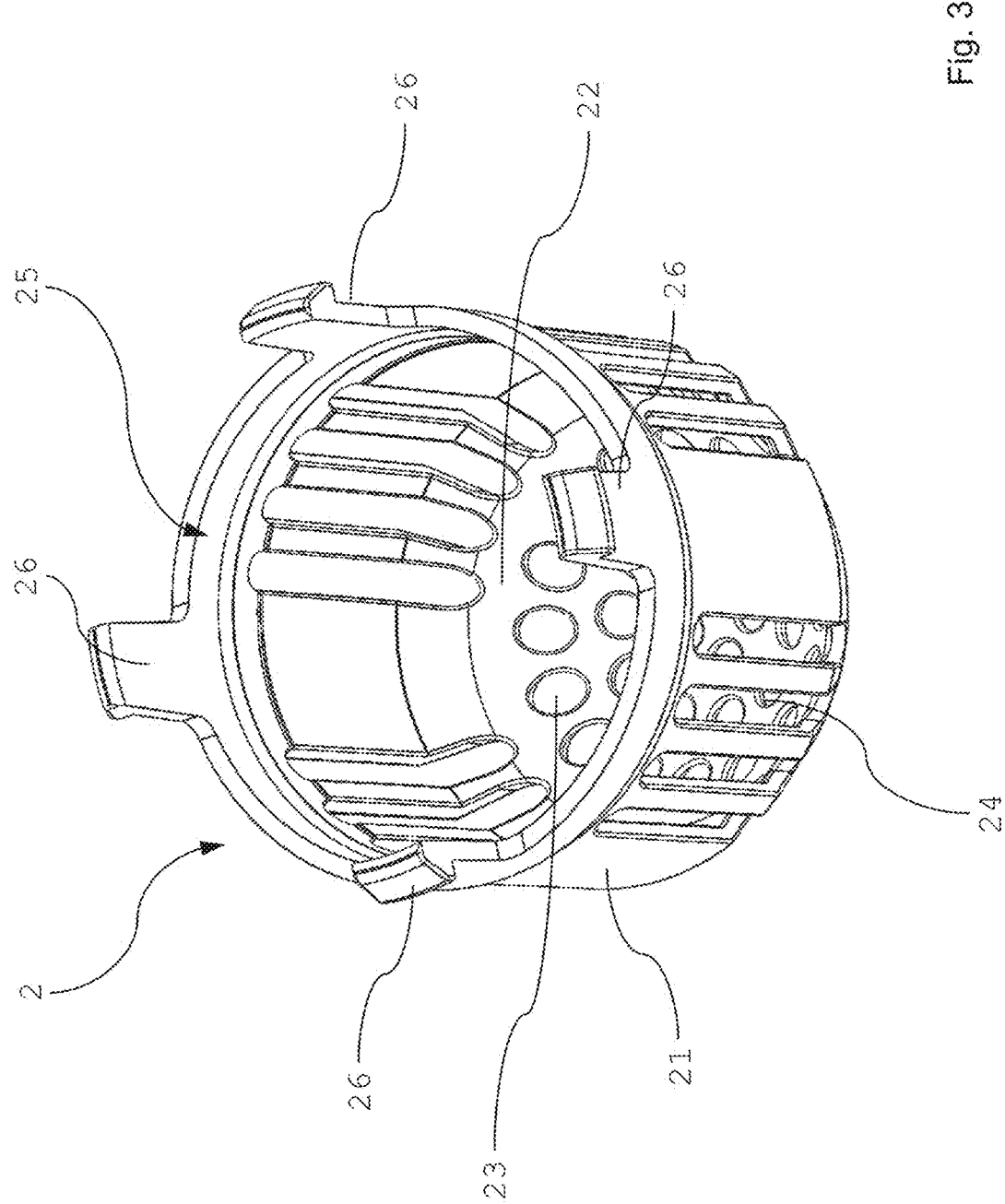
FIG. 3 is a perspective view of the containment element of the container of FIG. 1.

Containment element 2 of the embodiment of container 1 shown in FIG. 1 is shown in more detail in FIG. 3. Containment element 2 comprises a tubular section 21 which has a generally circular cross-section, and a bottom 22 which convexly protrudes towards the outside at the distal end of tubular section 21. Bottom 22 is provided with a number of apertures in form of through-holes 23 and slots 24. Slots 24 extend from a transition of bottom 22 into tubular section 21 of containment element 2 and towards the proximal end of containment element 2. Through-holes 23 and slots 24 allow for a continuous flow of treatment liquid into and out of containment element 2 and around an ophthalmic lens (e.g. a soft contact lens) contained therein (the lens not being shown in the drawings). Tubular section 21 of containment element 2 has a proximal end 25 remote from the bottom 22. At this proximal end 25 tubular section 21 four latches 26 (latching tabs) are arranged which protrude from the proximal end 25 of the tubular section 21 towards the distal end of the mounting element 3. The four latches 26 are circumferentially arranged around the longitudinal axis 11 of the container 1 at an equal distance from the longitudinal axis 11. Adjacent latches 26 are arranged at an angular displacement of 90° relative to one another. In the assembled state of container 1, latches 26 are in engagement with corresponding orifices 32 arranged in the sidewall of mounting element 3.

At least on an inner surface of the containment element 2 the through-holes 23 and slots 24 open out into the inner surface of the bottom 22 with rounded edges (not exaggeratedly shown in the drawings).

Figure 4:
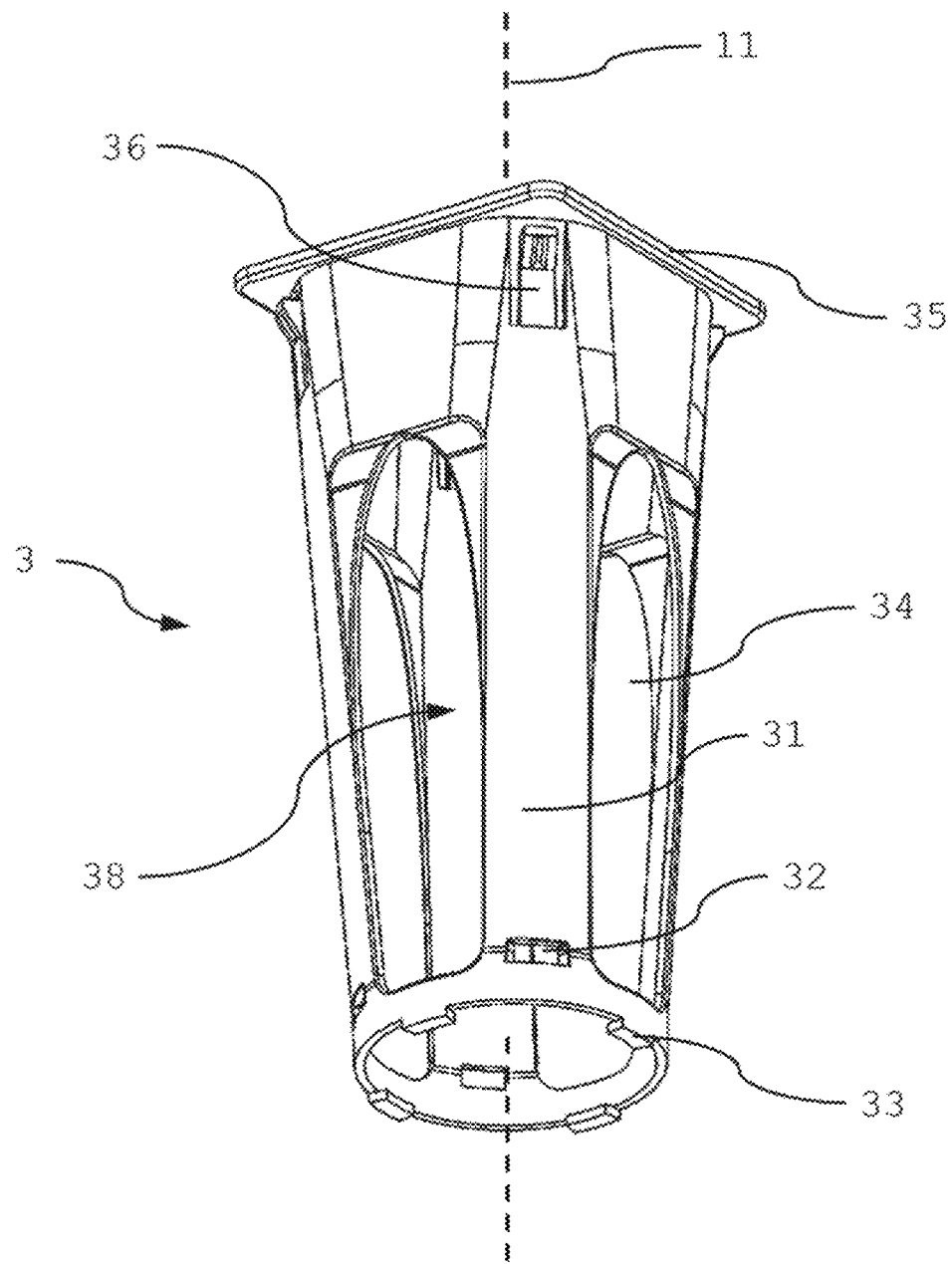
FIG. 4 is a perspective view of the mounting element of the container of FIG. 1.

Mounting element 3 of container 1 shown in FIG. 1 is shown in more detail in FIG. 4, and comprises sidewall 31 extending along the longitudinal axis 11 of the container 1. Mounting element 3 further comprises an access opening 37 arranged at the proximal end of mounting element 3 remote from the containment element 2 and defines an access to an inner space 38 of mounting element 3. Sidewall 31 is provided with four elongated flow openings 34 arranged at an equal distance from longitudinal axis 11 and at an angular displacement of 90° relative to one another. Flow openings 34 are tapering towards their proximal end, (i.e. in the direction towards the access opening 37 of the mounting element 3). As can be seen in FIG. 4, the elongated flow openings at their proximal end have an elliptic shape, but may have a different tapering shape as well.

In the sidewall 31 of mounting element 3 four orifices 32 are provided which in the assembled state of container 1 are in engagement with the latches 26 of containment element 2 so as to lock the elements in place. The four orifices 32 correspond to the four latches 26 of containment element 2 and are circumferentially arranged around the longitudinal axis 11 of the container 1 at an equal distance from the longitudinal axis 11. Adjacent orifices 32 are arranged at an angular displacement of 90° relative to one another.

For additional fixation of retaining element 4 in the assembled container 1, mounting element 3 has four lugs 33 protruding in longitudinal direction from the distal end of mounting element 3 towards the proximal end 25 of tubular section 21 of containment element 2. The four lugs are circumferentially arranged around the longitudinal axis 11 of the container 1 at an equal distance from the longitudinal axis 11, and adjacent lugs 33 are arranged at an angular displacement of 90° relative to one another.

At the proximal end of mounting element 3, surrounding the access opening 37, mounting element 3 is provided with a flange 35 having a square shape. Resilient locking tabs 36 are arranged beneath the square shaped flange 35 (at the corners of the square).

The square flange 35 and the resilient locking tabs 36 serve for secure attachment of the container 1 to a transport carrier as will be described in more detail below. This square shape of the flange 35 is advantageous with respect to an arrangement of a plurality of containers 1 next to each other in an elongated web of a transport carrier. As can be easily understood, however, the shape of the flange 35 may generally vary without affecting its function.

Figure 5:
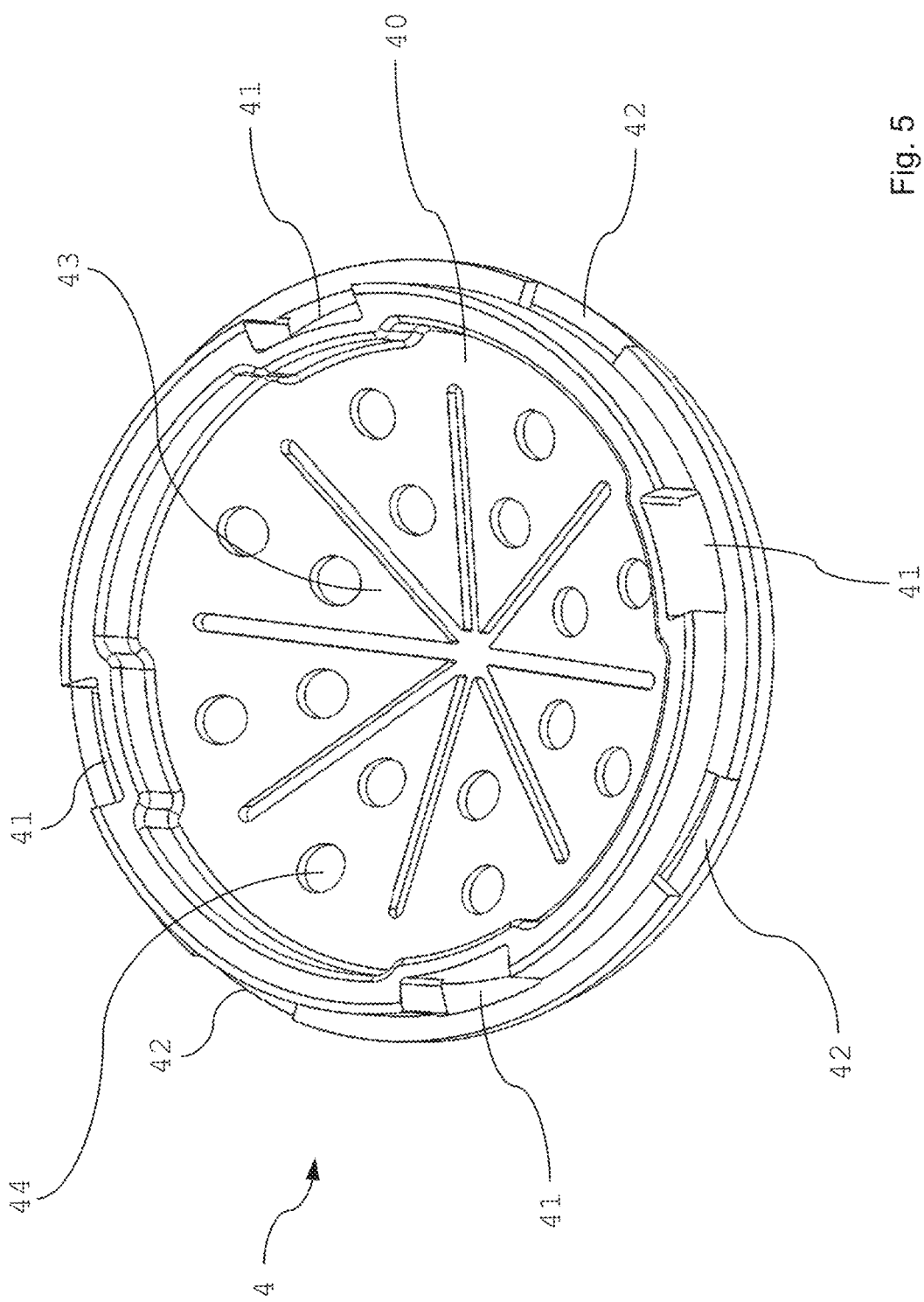
FIG. 5 is a perspective view of the retaining element of the container of FIG. 1.

In FIG. 1 retaining element 4 is shown fixedly mounted in the assembled container 1 in between containment element 2 and mounting element 3. Retaining element 4 is shown in more detail in FIG. 5. Retaining element 4 comprises a diaphragm 40 having flexible fins 43 which extend from a circumferential cylindrical portion towards the center of the diaphragm. Flexible fins 43 are slightly inclined towards the bottom 22 of containment element 2 and are provided with fin through-holes 44 enabling free passage of treatment liquid into and out of containment element 2 (which in operation contains the lens to be treated, not shown in the drawings). Instead of the fins 43, narrow spokes may also be provided to increase the flow of treatment liquid into and out of containment element 2 as long as the spokes are adapted to securely retain the lens in containment element 2 during transport of container 1 through the liquid.

Retaining element 4 has a circular shape and has four through-holes 41 arranged in a circumferential portion of the retaining element 4 for allowing latches 26 of containment element 2 to extend through the through-holes 41 of retaining element 4. Latches 26 hold the retaining element 4 in position during and after assembly of container 1. For additional fixation of retaining element 4 in the assembled state of the container 1, mounting element 3 has four lugs 33 protruding from the distal end of mounting element 3 in longitudinal direction towards the proximal end 25 of tubular section 21 of containment element 2, and retaining element 4 additionally has four indentations 42 arranged in a circumferential portion of the retaining element 4, with the lugs 33 of the mounting element 3 engaging into the indentations 42 of the retaining element 4 when container 1 is assembled.

To assemble container 1, the retaining element 4 is placed onto the containment element 2 such that latches 26 of containment element 2 are passed through through-holes 41 of retaining element 4. Retaining element 4 and containment element 2 are then pre-assembled. Subsequently, latches 26 of containment element 2 are introduced into the distal end of the mounting element 3 until they engage into the orifices 32 arranged in sidewall 31 of mounting element 3 (the latches 26 snap into the orifices 32). At the same time, the lugs 33 of mounting element 3 engage into the indentations 42 of retaining element 4, thus securely fixing retaining element 4 between containment element 2 and mounting element 3. No retainer ring or any other fixation element is necessary to fixedly arrange retaining element 4. Container 1 is then assembled.

Retaining element 4 separates the inner space 38 of mounting element 3 from the inner space of containment element 2 accommodating the lens. Mounting element 3 is at least partly open laterally (elongated flow openings 34), and is also open at the proximal end (access opening 37). Containment element 2, however, is essentially closed (tubular section 21, convex bottom 22, retaining element 4), so that the lens accommodated in the inner space of containment element 2 cannot get lost during the transport through one or more liquid baths. At the same time, the lens is allowed to freely float within the inner space of containment element 2 so as to be continuously and completely exposed to the treatment liquid of the respective bath.

As has been described already, mounting element 3 extends along the longitudinal axis of the container 1 from the access opening 37 to the proximal end 25 of the tubular section 21 of containment element 2 so as to enable introduction of the containment element 2 of another such container 1 into the mounting element 3 through access opening 37 to achieve a stacked arrangement of containers 1. To allow for easy introduction, the sidewall 31 of the mounting element 3 is conically tapering.

Figure 6:
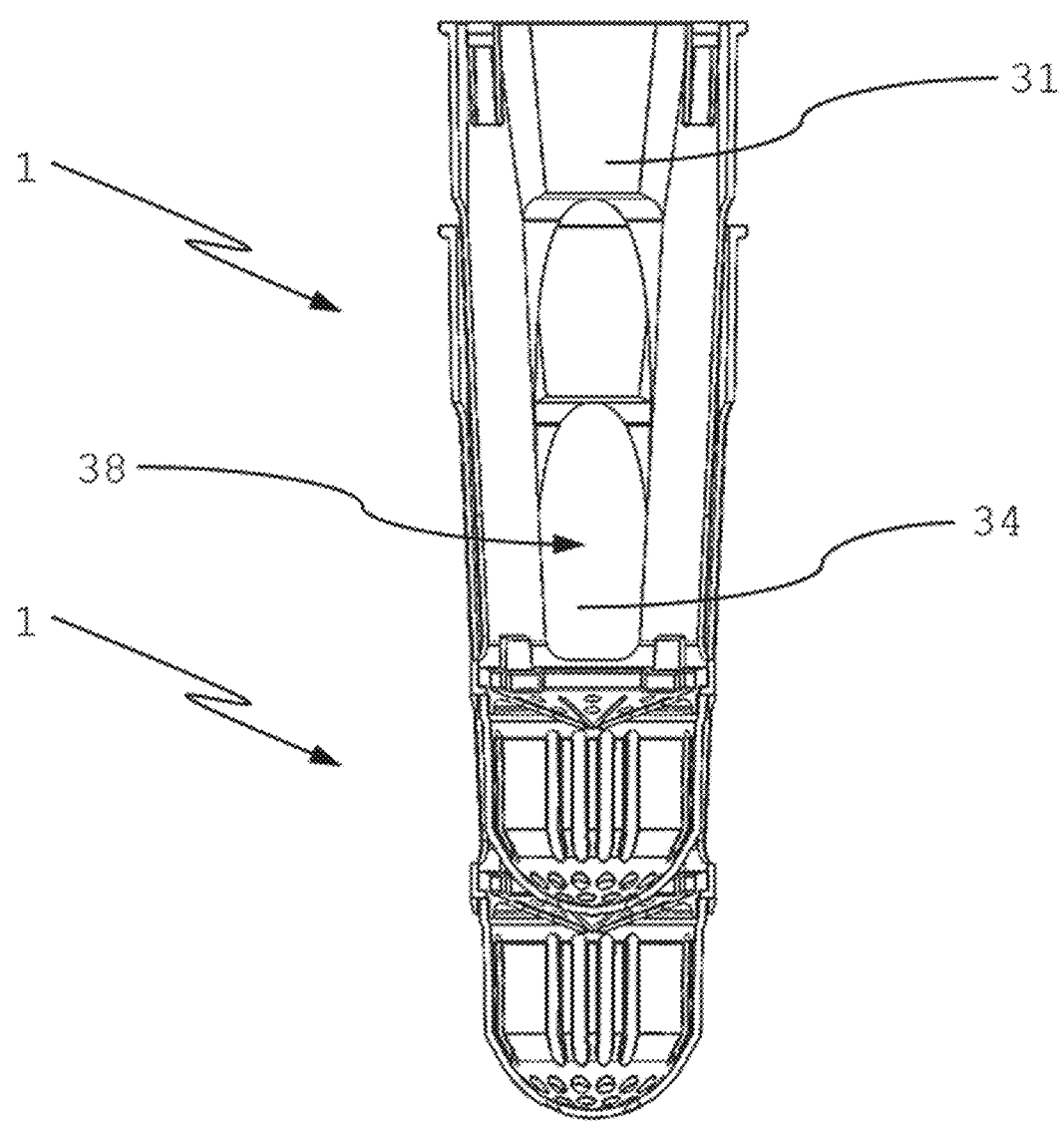
FIG. 6 is a side view of two stacked containers.

FIG. 6 shows two such stacked containers 1. It is evident, that even in this stacked arrangement of containers 1 treatment liquid can easily enter into the inner space of the containment elements 2 of each of the stacked containers 1 in which the lenses to be treated are accommodated. The treatment liquid may enter into the inner space of containment element 2 of the "inner" container 1 through the flow openings 34 of the "outer" container 1 and through the openings 23 and slots 24 of the containment element 2 of the "inner" container 1. As regards the "outer" container 1, liquid can enter into the inner space of containment element 2 of the "outer" container 1 through the openings 23 and slots 24 of the containment element 2 of "outer" container 1. Thus, the lens contained in the inner space of the "inner" container 1 ad well as the lens contained in the "outer" container are sufficiently exposed to the treatment liquid.

Lenses can be introduced into and removed from the containment element 2 of the respective container 1 with the aid of a conventional gripper. For introduction of a lens into the containment element 2, the gripper with the lens attached thereto is moved downwardly and the flexible fins 43 of retaining element 4 are bent downwardly towards bottom 22 of the containment element. Once the gripper has released the lens and has been retracted, the flexible fins 43 return to their original position, thus closing containment element 2 and preventing the lens from escaping from the containment element 2 during the transport through the liquid bath. Similarly, for removal of the lens from the containment element 2, the lens can be gripped by the gripper and can then be removed from the containment element 2.

The material retaining element 4 including diaphragm 40 is made of is selected in accordance with the treatment liquids used for treatment of the contact lenses and also depending on the required mechanical (elastic, resilient) properties thereof. By way of example, a suitable material is silicone.

Similarly, containment element 2 as well as mounting element 3 can be made of a material which his suitable for use in the treatment liquids and which is also suitable from a manufacturing point of view. A suitable material may be an injection-moldable plastic material such as a polyolefin, PET, or may be any other suitable material. By way of example, containment element 2 and mounting element 3 may be made from polypropylene, which allows for a reliable and cost-effective manufacturing of these elements through injection-molding and which is suitable for use in the treatment liquids.

As can be seen further from FIG. 6, the sidewall 31 extends along the longitudinal axis and is conically tapering. The slight conical taper of the sidewall 31 is advantageous in that upon insertion of a container 1 into a through-hole 51 of a transport carrier 5 from above, see FIG. 7 (showing a transport carrier assembly comprising two such transport carriers 5 stacked one above the other), the container 1 snugly fits in the through-hole 52. As the resilient locking tabs 36 slide past the interior walls surrounding the through-holes 52 of transport carrier 5 the resilient locking tabs 36 snap outwardly and lock the container 1 to the transport carrier 5 at the desired position. This snap fit can be released again by pressing the resilient locking tabs 36 inwardly thereby allowing for removal of the container 1 from the transport carrier 5.

As can be seen further from FIG. 7, each transport carrier 5 comprises a plurality of through-holes 51 arranged in the elongated web 50, and in each of the through-holes 52 a container 1 as described hereinbefore is arranged and is fixedly mounted to the transport carrier 5 in the manner explained above. Due to the very narrow space between adjacently arranged containers 1, the containers 1 can be mounted to the transport carrier 5 with the aid of a suitable mounting tool. When being mounted, the square-shaped flange 35 of mounting element 3 of the respective container 1 rests against the upper surface of elongated web 50 and prohibits the container 1 from slipping through the respective through-hole 52. The resilient locking tabs 36 right underneath the square-shaped flange 35 rest against the lower surface of the elongated web 50. The square shape of the sidewall 31 in the portion of mounting element 3 right beneath flange 35 fits into corresponding square-shaped through-hole 52 so that each container 1 is mounted at a desired position and with a desired orientation to the respective transport carrier 5.

As can be seen further from FIG. 7, each transport carrier 5 comprises two engagement portions 51 which are arranged at opposite ends of the elongated web 50 of the respective transport carrier 5 (only one engagement portion 51 being shown in FIG. 7) for engagement with a transport device (not shown) that moves the transport carriers 5 through the respective baths. Each transport carrier 5 further comprises an RFID (radio frequency identification) transponder 53. The RFID transponder 53 allows for identification of the respective transport carrier 5 and for detection of the position of the respective transport carrier 5 in the manufacturing line. As the programmable logic control (PLC) of the manufacturing line always knows what type of lens has been introduced into which container 1 of which transport carrier 5, it is always possible to determine what type of lens is contained in the individual containers 1 of the respective transport carrier 5.

As can be seen in FIG. 7, the containers 1 of the upper transport carrier 5 are inserted into the inner space 37 of the mounting element of the containers 1 of the lower transport carrier 5 such that the containment element 2 of the respective container 1 of the upper transport carrier 5 is completely inserted into the mounting element 3 of the respective container 1 of the lower transport carrier 5. However, as can also be seen in FIG. 6 and FIG. 7 and as is already explained above, the containment element 2 of the respective container 1 ("inner" container) of the upper transport carrier 5 is arranged in the mounting element 3 of the respective container 1 ("outer" container) of the lower transport carrier 5 such that access for the treatment liquid into the containment element 2 of the "inner" container 1 of the is established through the elongated flow openings 34 arranged in the sidewall 31 of the mounting element 3 of the respective "outer" container 1.

The transport carrier assembly shown in FIG. 7 ("piggyback" assembly) can be transported through the liquid bath in a manner well-known in the art. It goes without saying that it is within the scope of this invention to provide a transport carrier assembly with more than two carriers stacked one above the other which works in accordance with the principles already described above.

The container according to the invention can be used in a fully automated production processes for ophthalmic lenses such as, for example, soft contact lenses, in particular soft contact lenses made of a silicon hydrogel (SiHy) material. The container is simple in construction and capable of being manufactured reproducibly in mass production processes, for example by injection molding.

While embodiments of the invention have been described with the aid of the drawings, various changes, modifications, and alternatives are conceivable without departing from the teaching underlying the invention. Therefore, the invention is not intended to be limited to the described embodiments but rather is defined by the scope of the appended claims.

The invention claimed is:

1. Container (1) for accommodating an ophthalmic lens during a lens treatment process, the container having a longitudinal axis (11) and comprising as separate elements a containment element (2), a mounting element (3), and a retaining element (4),
   wherein the containment element (2) comprises a tubular section (21) and a bottom (22) arranged at a distal end of the tubular section (21), the bottom (22) protruding convexly towards the outside at the distal end of the tubular section (21) and being provided with a number of apertures (23, 24) for enabling a free flow of a treatment liquid into and out of the containment element (2), the tubular section (21) at a proximal end (25) thereof having a latch (26) protruding from the proximal end (25) of the tubular section (21) towards the mounting element (3),
   wherein the mounting element (3) comprises a sidewall (31) extending along the longitudinal axis (11) of the container (1), the sidewall (31) being provided with recesses or orifices (32) which are in engagement with the latch (26) of the containment element (2), and wherein the mounting element (3) further comprises an access opening (37) arranged at a proximal end of the mounting element (3),
   wherein the retaining element (4) is fixedly arranged in between the containment element (2) and the mounting element (3), the retaining element (4) being configured to prevent the ophthalmic lens from being washed out of the containment element (2) and to permit access for a gripper through the access opening (37) of the mounting element (3) into the containment element (2) for insertion and removal of the ophthalmic lens.

2. The container (1) according to claim 1, wherein the mounting element (3) further comprises a plurality of elongated flow openings (34) arranged in the sidewall (31) for allowing a treatment liquid to flow into and out of an inner space (38) of the mounting element (3).

3. The container (1) according to claim 2, wherein the elongated flow openings (34) are tapering, towards a proximal end thereof.

4. The container (1) according to claim 1, wherein the retaining element (4) comprises a through-hole (41) arranged in a circumferential portion of the retaining element (4), with the latch (26) of the containment element (2) extending through the through-hole (41) of the retaining element (4).

5. The container (1) according to claim 1, wherein the mounting element (3) has at least one lug (33) protruding in longitudinal direction from a distal end of the mounting element (3) towards the proximal end (25) of the tubular section (21) of the containment element (2), and wherein the retaining element (4) has at least one indentation (42) arranged in a circumferential portion of the retaining element (4), with the at least one lug (33) of the mounting element (3) engaging into the at least one indentation (42) of the retaining element (4).

6. The container (1) according to claim 3, wherein the retaining element (4) comprises a through-hole (41) arranged in a circumferential portion of the retaining element (4), with the latch (26) of the containment element (2) extending through the through-hole (41) of the retaining element (4).

7. The container (1) according to claim 3, wherein the mounting element (3) has at least one lug (33) protruding in longitudinal direction from a distal end of the mounting element (3) towards the proximal end (25) of the tubular section (21) of the containment element (2), and wherein the retaining element (4) has at least one indentation (42) arranged in a circumferential portion of the retaining element (4), with the at least one lug (33) of the mounting element (3) engaging into the at least one indentation (42) of the retaining element (4).

8. The container (1) according to claim 1, wherein the sidewall (31) of the mounting element (3) extends along the longitudinal axis of the container (1) from the access opening (37) to the proximal end (25) of the tubular section (21) of the containment element (2) and defines an inner space (38) of the mounting element (3) allowing for introduction of the containment element (2) of another such container (1) into the inner space (38) of the mounting element (3) of the container (1) through the access opening (37).

9. The container (1) according to claim 3, wherein the sidewall (31) of the mounting element (3) extends along the longitudinal axis of the container (1) from the access opening (37) to the proximal end (25) of the tubular section (21) of the containment element (2) and defines an inner space (38) of the mounting element (3) allowing for introduction of the containment element (2) of another such container (1) into the inner space (38) of the mounting element (3) of the container (1) through the access opening (37).

10. The container (1) according to claim 8, wherein the sidewall (31) of the mounting element (3) is arranged to conically taper towards the distal end of the mounting element (3).

11. The container (1) according to claim 1, wherein the mounting element (3) is provided with a flange (35) surrounding the access opening (37), the flange (35) having a square shape.

12. The container (1) according to claim 8, wherein the mounting element (3) is provided with a flange (35) surrounding the access opening (37), the flange (35) having a square shape.

13. The container (1) according to claim 11, wherein the sidewall (31) of the mounting element (3) is provided with at least one resilient locking tab (36) arranged beneath the flange (35).

14. The container (1) according to claim 1, wherein the retaining element (4) comprises a diaphragm (40) having flexible fins (43) which extend from a circumferential portion of the retaining element (4) towards a center of the diaphragm (40), and wherein the flexible fins (43) are inclined towards the bottom (22) of the containment element (2) and are provided with fin through-holes (44) for enabling free passage of treatment liquid into and out of the containment element (2).

15. The container (1) according to claim 1, wherein the apertures (23, 24) in the containment element (2) comprise bottom through-holes (23) and longitudinal slots (24), the longitudinal slots (24) extending from the bottom (22) into the tubular section (21) towards the proximal end of the tubular section (21) of the containment element (2).

16. The container (1) according to claim 3, wherein the apertures (23, 24) in the containment element (2) comprise bottom through-holes (23) and longitudinal slots (24), the longitudinal slots (24) extending from the bottom (22) into the tubular section (21) towards the proximal end of the tubular section (21) of the containment element (2).

17. The container (1) according to claim 1, wherein at least on an inner surface of the bottom (22) of the containment element (2) the apertures (23, 24) open out into the inner surface of the bottom (22) with rounded edges.

18. A transport carrier (5) comprising an elongated web (50) and two engagement portions (51) capable of engaging with a transport device, one of the two engagement portions (51) being arranged at one longitudinal end of the elongated web (50) and the other one of the two engagement portions (51) being arranged at the other end of the elongated web (50), the transport carrier (5) further comprising a plurality of adjacently arranged through-holes (52) in the elongated web (50), with a container (1) according to claim 1 being arranged in at least one of the through-holes (52) of the elongated web (50) of the transport carrier (5).

* * * * *

UNITED STATES PATENT AND TRADEMARK OFFICE
CERTIFICATE OF CORRECTION

PATENT NO. : 9,801,445 B2  
APPLICATION NO. : 15/274079  
DATED : October 31, 2017  
INVENTOR(S) : Roger Biel et al.

Page 1 of 1

It is certified that error appears in the above-identified patent and that said Letters Patent is hereby corrected as shown below:

On the Title Page

Item (72), in Column 1, in "Inventors", Line 1, delete "Roger Beil" and insert -- Roger Biel --.

Signed and Sealed this
Twenty-eighth Day of August, 2018

Andrei Iancu
*Director of the United States Patent and Trademark Office*